United States Patent [19]

Mon

[11] 4,381,002

[45] Apr. 26, 1983

[54] FLUIDIC-CONTROLLED OXYGEN INTERMITTENT DEMAND FLOW DEVICE

[75] Inventor: George Mon, Silver Spring, Md.

[73] Assignee: The United States of America as represented by the Secretary of the Army, Washington, D.C.

[21] Appl. No.: 217,881

[22] Filed: Dec. 18, 1980

[51] Int. Cl.$^3$ ............................................. A61M 16/00
[52] U.S. Cl. ........................... 128/204.24; 128/204.26; 137/812
[58] Field of Search ...................... 128/204.18, 203.28, 128/204.21, 204.24, 204.25, 204.26, 204.28, 205.24, 205.25, 207.18, 205.19, 205.13, 205.16, 205.17; 137/812

[56] References Cited

U.S. PATENT DOCUMENTS

| | | | |
|---|---|---|---|
| 3,324,891 | 6/1967 | Rhoades | 137/812 |
| 3,368,555 | 2/1968 | Beasley | 128/204.24 |
| 3,494,357 | 2/1970 | Kimball | 128/145.6 |
| 3,537,449 | 11/1970 | Foxwell et al. | 128/204.24 |
| 3,566,862 | 3/1971 | Schuh et al. | 128/30.2 |
| 3,754,550 | 8/1973 | Kipling | 128/205.16 |
| 3,949,749 | 4/1976 | Stewart | 128/204.24 |
| 3,957,047 | 5/1976 | Freytag et al. | 128/204.24 |
| 3,976,065 | 8/1976 | Durkan | 128/204.24 |
| 4,057,059 | 11/1977 | Reid, Jr. et al. | 128/204.24 |

OTHER PUBLICATIONS

Mon, *The Design of a Fluidic Oxygen Intermittent-Demand Flow Device*, Report No. HDL-TM-80-14, Mar. 1980, Harry Diamond Labs.

Auerbach et al., *A New Oxygen Cannula System using Intermittent-Demand Nasal Flow*, Chest, 74 (Jul. 1, 1978), 39-44.

Woodward et al., *Fluid Amplifier-Controlled Medical Devices*, Proceedings of IRES 17th Annual Conference on Engr. in Med. and Biol., Cleveland, OH (Nov. 16-17, 1964).

Joyce et al., *A Timed-Cycle External Cardiac Compressor*, Harry Diamond Laboratories, HDL-TM-68-35 (Dec. 1968).

Manion et al., Fluorics 33: *Design and Staging of Laminar Proportional Amplifiers*, Harry Diamond Laboratories, HDL-TR-1608 (Sep. 1972).

Mon, *Laminar Proportional Amplifier*, Proceedings of Sixth Cranfield Fluidics Conference, Cambridge, U.K. (Mar. 1974).

Mon, *The Basic Design Concepts of Laminar Proportional Amplifiers with Positive Feedback*, Journal of Dynamic Systems, Measurements, and Control, Trans. ASME (Mar. 1979), 77-80.

*Primary Examiner*—Henry J. Recla
*Attorney, Agent, or Firm*—Nathan Edelberg; Robert P. Gibson; Saul Elbaum

[57] ABSTRACT

The apparatus of the present invention comprises means for regulating intermittent flow of respiratory fluid to a patient during oxygen therapy. The invention utilizes laminar fluidic elements in the control circuit for regulating the operation of an oxygen flow valve.

6 Claims, 4 Drawing Figures

FLUIDIC-CONTROLLED OXYGEN INTERMITTENT DEMAND FLOW DEVICE

RIGHTS OF THE GOVERNMENT

The invention described herein may be manufactured, used and licensed by or for the U.S. Government for governmental purposes without payment to me of any royalty thereon.

BACKGROUND OF THE INVENTION

Oxygen therapy has been traditionally administered utilizing apparatus which provides a continuous flow of oxygen to the patient. The continuous flow technique wastes a great deal of oxygen due to the fact that inspiration, or inhalation, occurs only during approximately one third of the breathing cycle. The oxygen which continues to flow during the expiration portion of the breathing cycle is simply expelled into the atmosphere. It is therefore desireable to provide means for supplying a flow of oxygen to the patient only during the inspiration portion of the cycle.

Intermittent flow for oxygen therapy has been shown by Auerbach et al. (D. Auerbach et al., A New Oxygen Cannula System Using Intermittent Demand Nasal Flow, CHEST, 74, July 1, 1978, pages 39-44) to be an effective way of conserving oxygen and reducing its cost to the patient. By using a prototype of an intermittent demand flow device, described in the above cited article, Auerbach et al. projected a possible savings of $744.60 per year per patient at a flow rate of two liters per minute. For thousands of users at home alone, this represents a savings of millions of dollars anually. Additional significant savings could be realized for in-patient care at hospitals.

To follow the patients respiratory cycle, the intermittent demand device must be able to sense very small negative and positive pressures in or near the nostrils via a nasal cannula or a face mask. The Auerbach et al device utilizes a spring loaded diaphragm to sense these pressures. Because the diaphragm is necessarily very sensitive to extremely low pressures ($\pm 0.2$ millimeters Hg) it is by necessity very delicate, requiring extremely fine balancing. Such a diaphragm is extremely sensitive to external forces, such as vibration. The Auerbach et al device is reported to operate without failure for over 150 hours, too short a time for the intended usage.

It is an object of this invention to provide an intermittent demand device suitable for use in oxygen therapy which is highly dependable for greatly extended periods of time.

It is an object of this invention to provide such a device which is, in addition to being dependable, extremely sensitive to the patients respiratory cycle.

It is yet another object of this invention to provide an intermittent flow device which operates quietly and without any disturbing noise.

It is still another object of this invention to provide an intermittent flow device for oxygen therapy which consumes less oxygen than the known intermittent flow device of the prior art.

SUMMARY OF THE INVENTION

The intermittent flow device of the present invention comprises one or more pure fluid amplification devices for controlling the intermittent flow of oxygen to a patient. The fluidic devices of the present invention are responsive to the patients respiratory cycle, and control valve means which intermittently halts the flow of oxygen to the patient.

DESCRIPTION OF A PREFERRED EMBODIMENT

Fluidics has been applied in the design of medical devices, such as heart pumps, cardiac compressors, and respirators. The fluidic components used in these prior art medical devices are of the turbulent flow type, having a high rate of power consumption and a low signal to noise ratio. The application of these fluidic devices to medical apparatus has been very successful. Since the fluidic devices have no moving parts, they are highly reliable. However, it has been found that the turbulent flow fluidic devices are not suitable for use in an intermittent demand valve because of their high rate of power consumption and high level of flow noise. The high power consumption would consume too great an amount of oxygen, and the relatively high flow noise would be objectionable at home and in the hospital. Additionally, the low signal to noise ratio would make it difficult or impossible to provide the necessary sensitivity for a demand flow apparatus.

The present invention overcomes these shortcomings of the turbulent flow fluidic devices by utilizing laminar flow elements. Because of the laminar flow through the elements, these devices have a power consumption approximately three orders of magnitude less than that of the turbulent flow devices, a very low noise output, and an extremely high signal to noise ratio.

Figure 1:
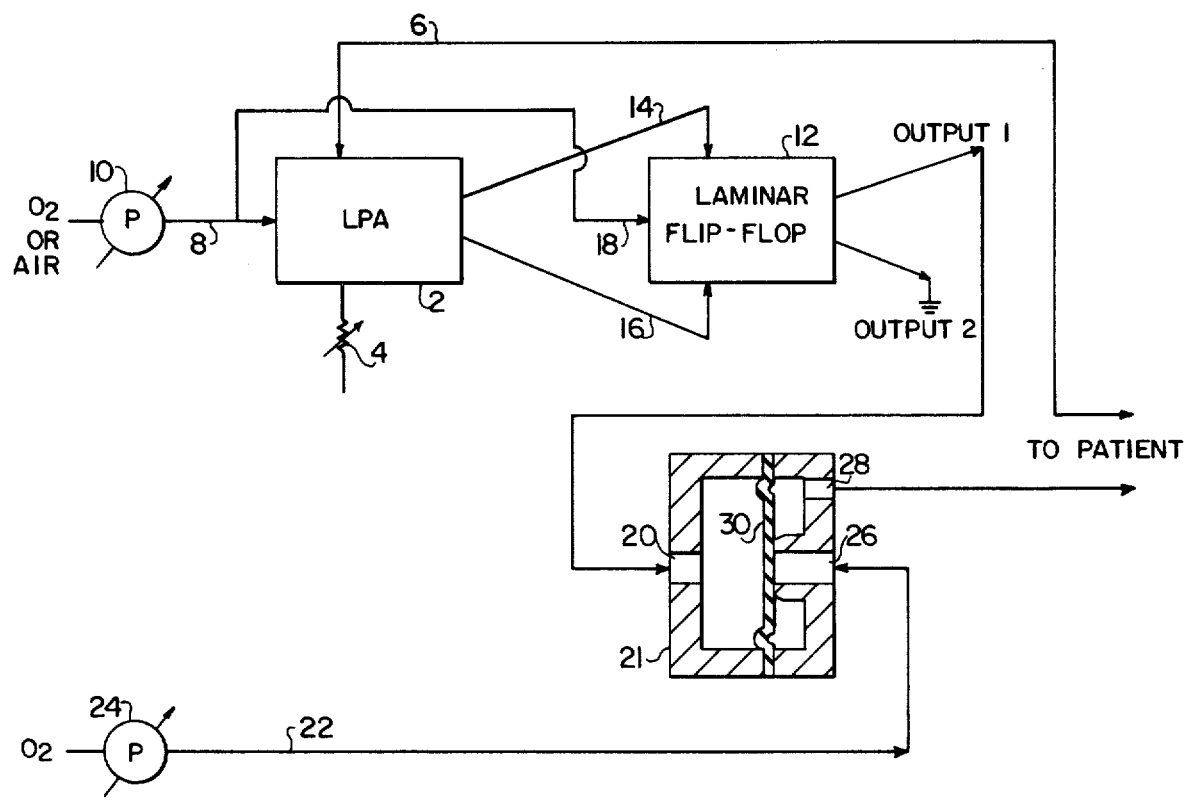
FIG. 1 schematically illustrates a preferred embodiment of the present invention.

FIG. 1 schematically illustrates a preferred embodiment of the present invention. Pure oxygen, or any other respiratory fluid, is fed through line 22 to the input 26 of valve 21. Pressure regulator 24 regulates the pressure of the oxygen flowing through line 22. Diaphragm 30 in the valve 21 is operative to open and close the passage 26. When the diaphragm separates from the opening 26, oxygen flows through outlet 28 to the patient.

Sensing line 6 extends from the face mask or cannula of the patient to the control means of the present invention. The present control means, rather than being a spring biased diaphragm valve as in the prior art device, comprises a fluidic laminar proportional amplifier 2. A power flow of fluid to the laminar proportional amplifier (LPA) is provided through inlet 8 and pressure regulator 10. The power fluid to the control device may be oxygen, but an even greater savings may be achieved by using compressed air for the control portion of the circuit. Since the power consumption for the control circuit is relatively small, a fishtank pump or other small, low cost pneumatic supply can be used to power the fluidic circuit.

Sensing line 6 is connected of the two control port inlets of the LPA, while an adjustable biasing means 4 is connected with one end to the other control input and the other end in fluid communication with the atmosphere. The biasing means 4 is utilized to balance the output of the LPA between the two outputs 14 and 16 thereof in the absence of a signal from line 6. When a positive or negative pressure signal is applied through line 6 to the LPA as a result of the patients breathing cycle, the power flow of the LPA will be deflected toward one or the other of outputs 14 and 16.

The outputs 14 and 16 are connected to the control port inputs of laminar flip-flop 12. The flip-flop is a laminar bi-stable fluid amplifier. The power flow to the flip-flop is provided through inlet 18. The output from the flip-flop will exit entirely through either output 1 or output 2, as shown in FIG. 1. When the flow is through output 1, such flow will enter valve 21 through the inlet 20 thereof, biasing the diaphragm 30 to close the oxygen inlet 26. Output 2 from the flip-flop is merely vented to the atmosphere. When the flow from the flip-flop is through outlet 2, the diaphragm 30 can be biased to an open position by the pressure of the oxygen at inlet 26, thereby allowing flow to the patient.

The intermittent demand apparatus of the present invention operates as follows. The flip-flop is initially biased so that the output thereof is through output 1. This pressure through inlet 20 of the valve 21 causes diaphragm 30 to shut off the oxygen flow to the patient. When the patient initiates the inspiration cycle, his effort generates a negative pressure signal which is sensed by the LPA via the sensing line 6. The LPA amplifies the pressure signal, deflecting the power flow through the LPA toward output 14. This causes the flow through bi-stable flip-flop 12 to be deflected toward output 2. The pressure in the valve 21 is thereby relieved, allowing the diaphragm flow valve to open, thereby permitting the oxygen to flow to the patient. This valve remains in its open position as long as the patient is inhaling. As soon as the patient begins the expiration cycle, a positive pressure is detected by the LPA through sensing line 6. The signal is amplified by the LPA, deflecting the flow through the LPA toward output 16. This in turn deflects the flow through the bi-stable flip-flop toward output 1. The flow through output 1 again pressurizes valve 21 to close the inlet 26, thus completing the cycle.

Regulator 10 controls the pressure of flow to the fluidic control circuit, while regulator 24 controls the pressure of oxygen flow to the patient. The bias control valve 4 is utilized to adjust the level of the switching pressure, or the sensitivity of the control circuit. It is possible to allow a small amount of oxygen to continue to flow to the patient during the expiration cycle, if this is deemed desireable. To accomplish this result, the diaphragm flow valve 21 can be partially opened by adjusting the pressure of the oxygen in line 22 to be slightly higher than the pressure of the flow through output 1. This low level of flow during the expiration cycle flushes the nasal dead space with oxygen at the beginning of inspiration.

As shown in FIG. 1, the control circuit and the oxygen flow path of the pressed apparatus are isolated by the diaphragm 30. Therefore, the control circuit can be powered either by the oxygen or by a much cheaper fluid such as compressed air. As noted above, this can be achieved by the use of a small low powered fish pump, or a similar device, and results in an even greater savings of oxygen.

Figure 2:
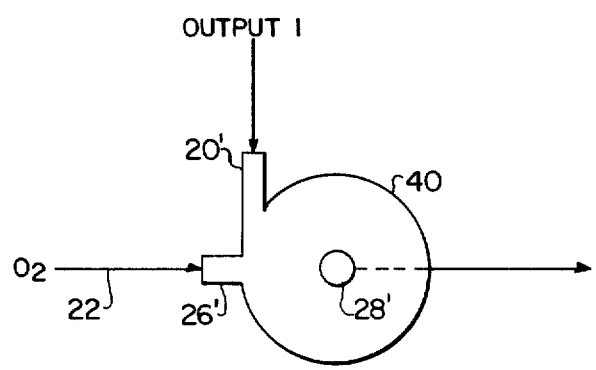
FIG. 2 illustrates an alternate embodiment for the oxygen flow control valve of FIG. 1.

FIG. 2 illustrates an alternate embodiment of the oxygen flow control valve 21 of FIG. 1. The device of FIG. 2 is a vortex valve, a fluidic device having no moving parts. If the valve of FIG. 2 is utilized in place of the valve 21 of FIG. 1, the resulting system would have no moving parts whatsoever.

The vortex valve 40 of FIG. 2 comprises a radially disposed inlet 26'. Oxygen continually enters inlet 26' through line 22. The flow from the control circuit output 1 enters the fluidic valve tangentially through inlet 20'. Centrally disposed outlet 28' permits the oxygen to flow to the patient. As is well known in the art of fluidics, in the absence of a signal through inlet 20', the oxygen entering the valve radially through inlet 26' will flow directly toward the centrally disposed outlet 28' and, in a relatively unimpeded fashion, exit the valve through the outlet. When a power flow enters the vortex valve through inlet 20', the tangential flow intercepts the flow of oxygen through inlet 26', thus generating a rapid vortical flow within the vortex chamber. The rapid vortical flow causes centrifugal force which prevents the fluid in the vortex chamber from reaching the outlet 28'. The result is that the oxygen flow through outlet 28 to the patient is effectively cut off. In utilizing the valve shown in FIG. 2, it is advisable to utilize oxygen as the control fluid, as the control fluid becomes mixed with the oxygen from line 22.

Figure 3:
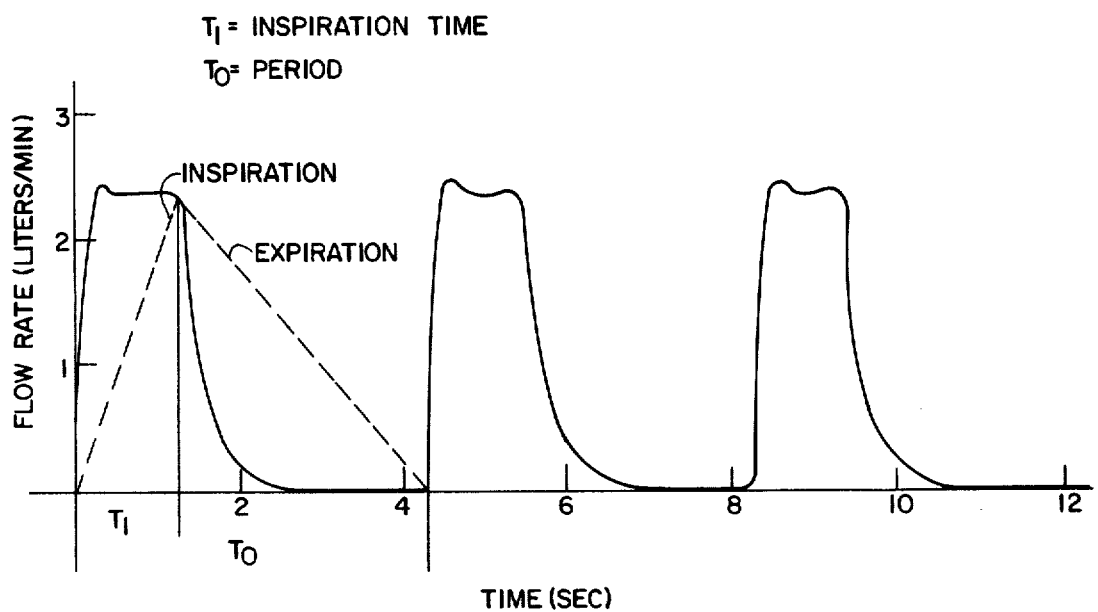
FIG. 3 is a graphical illustration showing the relationship between the patients breathing cycle and the flow of oxygen to the patient, utilizing the apparatus of the present invention.

FIG. 3 shows a typical trace of the oxygen flow to the patient during inspiration and expiration. The flow of oxygen rapidly increases to a maximum at the commencement of the inspiration cycle, rapidly dropping off to zero flow upon commencement of expiration. The result is virtually no oxygen flows during the time that the patient is exhaling.

Conservation of oxygen is one of the most important performance characteristics of the intermittent demand valve. The percentage of savings is defined as:

$$\text{Percent Savings} = \left(1 - \frac{Q + Q_c}{Q_p}\right) \times 100$$

where
Q=flow to patient (liters/min)
$Q_c$=flow to control circuit (liters/min)
$Q_p$=continuous flow to patient (liters/min)
The flow to the patient can be calculated by integrating the flow curve for each cycle and dividing by the period, t. To simplify the calculation, the flow to the patient can be approximately by setting $Q = \frac{1}{3} Q_p$ so that the above equation can be written as:

$$\text{Percent Savings} = \left(\frac{2}{3} - \frac{Q_c}{Q_p}\right) \times 100$$

Figure 4:
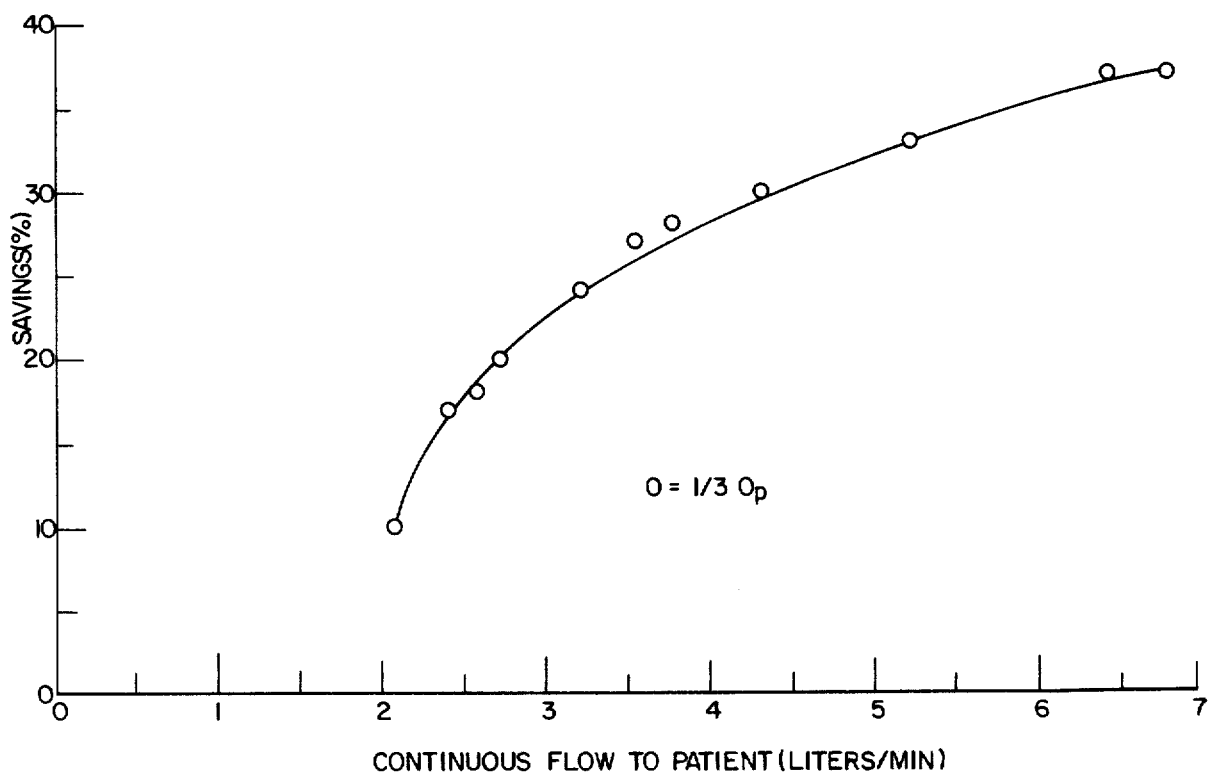
FIG. 4 graphically illustrates the degree of savings possible, as a function of continuous flow rate to the patient, which may be achieved by utilizing the apparatus of the present invention.

FIG. 4 shows a typical plot of the percentage of savings at various values of $Q_p$ when using oxygen as the control fluid. When the control circuit is powered by an external compressed gas source, such as a fish tank pump, $Q_c$ becomes zero, and the savings can be as high as 67%.

The intermittent demand flow device of the present invention may be advantagiously used in oxygen therapy. While achieving a greater savings of oxygen than the prior art device, the apparatus of the present invention is also extremely dependable as a result of the use of control elements having no moving parts. While the invention has been described with reference to the accompanying drawings, I do not wish to be limited to the details shown therein as obvious modifications may be made by those of ordinary skill in the art.

I claim:

1. An apparatus for providing intermittent flow of respiratory fluid to an individual, comprising:
   a supply of respiratory fluid;
   fluid application means for applying said respiratory fluid to a respiratory orifice of the individual;
   respiratory fluid communication means for providing a flow of said respiratory fluid from said respiratory fluid supply to said fluid application means;
   valve means, placed in said respiratory fluid communication means for interrupting said flow of respiratory fluid;
   a laminar bi-stable amplifier for controlling the operation of said valve means, including an inlet, a first outlet, a second outlet, a first control port, and an opposite second control port;
   an atmospherically biased laminar proportional amplifier for controlling the operation of said laminar bi-stable amplifier, including an inlet, a first outlet, a second outlet, a first control port, and an opposite second control port;
   a source of low pressure power fluid;
   power fluid supplying means for providing a flow of said power fluid from said power fluid source into the inlets of the laminar proportional amplifier and the laminar bi-stable amplifier, respectively;
   pressure sensing means for sensing a pressure at said respiratory orifice of the individual;
   pressure communication means for communicating said sensed pressure to the first control port of said laminar proportional amplifier;
   fluid communication bias means for atmospherically biasing said laminar proportional amplifier by communicating an atmospheric pressure flow to the second control port of said laminar proportional amplifier,
   wherein whenever said sensed pressure falls to an inhalation pressure indicating the initiation of an inspiration cycle by said individual, said sensed inhalation pressure communicated to said first control port of the laminar proportional amplifier and said atmospheric pressure communicated to said second control port of the laminar proportional amplifier comprise a first difference signal which causes said power fluid to flow from the inlet to the first output of said laminar proportional amplifier, and
   whenever said sensed pressure rises to an exhalation pressure indicating the initiation of an expiration cycle by said individual, said sensed exhalation pressure communicated to said first control port of said laminar proportional amplifier and said atmospheric pressure communicated to said second control port of the laminar proportional amplifier comprise a second difference signal which causes said power fluid to flow from the inlet to the second output of said laminar proportional amplifier;
   amplifier control fluid communication means for connecting the first and second control ports of the laminar bi-stable amplifier to the first and second outputs of the laminar proportional amplifier, respectively, so that switching of the power fluid between the two outputs of the laminar proportional amplifier in response to said first and second difference signals causes corresponding switching of the power fluid between the two outputs of the laminar bi-stable amplifier; and
   valve control fluid communication means for connecting at least one output of the laminar bi-stable amplifier in fluid communication with said valve means, wherein said valve means is controlled by the laminar bi-stable amplifier to open whenever said sensed pressure falls to said inhalation pressure and to close whenever said sensed pressure rises to said exhalation pressure.

2. An apparatus, as recited in claim 1, wherein the first output of said laminar bi-stable amplifier is connected in fluid communication with said valve means, and the second output of said laminar bi-stable amplifier is connected in fluid communication with the atmosphere.

3. An apparatus, as recited in claim 1, further comprising means for adjusting said first difference signal and said second difference signal.

4. An apparatus, as recited in claim 3, wherein said means for adjusting comprises a variable fluidic resistor placed in said fluid communication bias means.

5. An apparatus, as recited in claim 4, wherein said valve means comprises a diaphragm valve disposed in said fluid communications means for providing a flow of said respiratory fluid from said respiratory fluid supply to said fluid application means wherein said flow of respiratory fluid maintains said diaphragm valve in an open position and wherein an input from said laminar bi-stable amplifier causes said diaphragm valve to close, thus interrupting said flow of respiratory fluid to the individual.

6. An apparatus, as recited in claim 5, wherein said valve means comprises a vortex valve with a radial input in fluid communication with said source of respiratory fluid and a control output in fluid communication with said fluid application means and a tangential input in fluid communication with said first output of said laminar bi-stable amplifier whereby an input from said first output of said laminar bi-stable amplifier causes vortical flow in said vortex valve thereby interrupting said flow of respiratory fluid.

* * * * *